United States Patent [19]

Putzke

[11] 4,024,875
[45] May 24, 1977

[54] DEVICE FOR NON-INVASIVE PROGRAMMING OF IMPLANTED BODY STIMULATORS

[75] Inventor: James J. Putzke, New Hope, Minn.

[73] Assignee: Medtronic, Inc., Minneapolis, Minn.

[22] Filed: Sept. 19, 1975

[21] Appl. No.: 614,794

[52] U.S. Cl. .................. 128/419 PG; 128/419 PS; 128/423 R

[51] Int. Cl.² .......................................... A61N 1/36

[58] Field of Search ..... 128/419 C, 419 E, 419 PG, 128/419 PT, 419 R, 421, 422, 423, 2.1 A

[56] References Cited

UNITED STATES PATENTS

| | | | |
|---|---|---|---|
| 3,426,748 | 2/1969 | Bowers | 128/419 PG |
| 3,693,627 | 9/1972 | Berkovits | 128/419 PG |
| 3,727,616 | 4/1973 | Lenzkes | 128/419 E |
| 3,768,017 | 10/1973 | Dillman et al. | 128/2.1 A |

Primary Examiner—William E. Kamm
Attorney, Agent, or Firm—Lindquist & Vennum

[57] ABSTRACT

A device for the non-invasive programming of an implantable body stimulator. The device includes a power supply and circuitry for generating and transmitting a preselected number of pulses of radio frequency energy. A push-button switch initiates the operation of the pulse-generating circuitry and the power supply is enabled only during an interval of predetermined duration following the initiating of operation of the pulse-generating circuitry. In a preferred embodiment, the power supply includes a power source, such as batteries, and a voltage regulator for establishing a substantially constant supply voltage for all power source voltages above a preselected level. The device may include circuitry for indicating the establishment of the substantially constant supply voltage as well as circuitry for preventing the transmission of any programming pulses upon a failure to establish the substantially constant supply voltage level. The transmitted pulses may be employed to alter an output parameter of any implanted body stimulator and is described with reference to an alteration in the repetition rate of an implanted cardiac pacemaker.

18 Claims, 3 Drawing Figures

DEVICE FOR NON-INVASIVE PROGRAMMING OF IMPLANTED BODY STIMULATORS

BACKGROUND OF THE INVENTION

The output parameters of many prior art cardiac pacemakers are either present during fabrication, or established at the time of implant. With such pacemakers, adjustment of any output parameter requires a surgical exposure of the pacemaker itself. Other pacemakers are adjustable through the use of a needle-like tool.

More recently, various systems have been advanced for altering the output parameters of an implanted cardiac pacemaker with transmitted signals of electromagnetic energy. The pacemakers of these systems have included elements responsive to a preselected signal for altering at least one output parameter of the pacemaker on the occurrence of the signal. For example, in U.S. Pat. No. 3,311,111, the use of bistable magnetic reed switches is proposed for the control of pulse rate, voltage, current or duration as well as a selection of alternate output paths or leads. Other systems have been proposed in which pulsed signals are used to advance a counter, the accumulated count in the counter serving to establish the value of the output parameter or parameters to be altered. Pulses in this latter system may be magnetic or bursts of radio frequency energy, for example.

Variations in the "pulsed signal" systems described above have been proposed to reduce the possibility of an alteration in an output parameter of an implanted body stimulator via an extraneous signal. For example, in U.S. Pat. No. 3,805,796 there is disclosed a system having a first counter which advances in response to all detected pulse signals while a second counter is advanced only in response to signals detected after the count of the first counter reaches a preselected value. The value of the count in the second counter is employed to control at least one alterable output parameter. Thus, extraneous signals which are incapable of advancing the first counter to the preselected value cannot result in an alteration of the output parameter of the implanted device. Other systems have been proposed in which a first signal, a magnetic field, for example, enables the implanted device to respond to pulse signals for alteration of an output parameter in predetermined correspondence with the number of pulse signals. An example of such a system is disclosed in co-pending application Ser. No. 584,131 of John M. Adams and Clifton A. Alferness for Programmable Body Stimulator, filed June 5, 1975, which is co-owned with the present application.

From the above, it is apparent that much attention has been directed to providing implantable devices with alterable output parameters and to reducing the probability of an accidental output parameter alteration as a result of extraneous noise. It is contemplated that any desired output parameter alteration will be effected in a doctor's office and, preferably with a portable, non-invasive programming unit. It is therefore desirable that any programming unit have the capability of reliably generating and transmitting the desired number of signals with a minimum drain on the unit power supply. Additionally, it is desirable that such a unit have the ability to indicate the adequacy of the power supply and prevent the transmission in the event that the power supply voltage level is below an adequate level.

SUMMARY OF THE PRESENT INVENTION

The present invention provides a non-invasive programming device for altering at least one output parameter of an implanted body stimulator through the generation and transmission of a preselected number of pulses of radio frequency energy. The device includes a power supply, means for generating a preselected number of transmitted pulses of radio frequency energy and means for initiating the operation of the generating means. The power supply consists of a power source and a voltage regulator for establishing a substantially constant supply voltage for all power source voltage levels above a predetermined level. The voltage regulator is enabled only during an interval of predetermined duration following the initiating of operation of the generating means and the device is provided with circuitry for indicating the establishment of the substantially constant supply voltage level. In a preferred embodiment, the transmission of the radio frequency bursts is prevented until the substantially constant supply voltage level is established.

From the above, it is apparent that the programming unit of the present invention minimizes the drain on the power supply by enabling the voltage regulator only during a period of time during which it is desired to transmit programming pulses to an implanted body stimulator. In addition, the device has the capability of indicating that the power supply voltage level is adequate to power the production and transmission of the desired number of programming pulses. In the event that the power supply is inadequate to reliably produce and transmit the desired number of programming pulses, the transmission of those pulses is prevented and that fact indicated to the treating physician by the failure of the device to indicate an adequate power supply voltage.

DETAILED DESCRIPTION OF THE DRAWINGS

Figure 1:
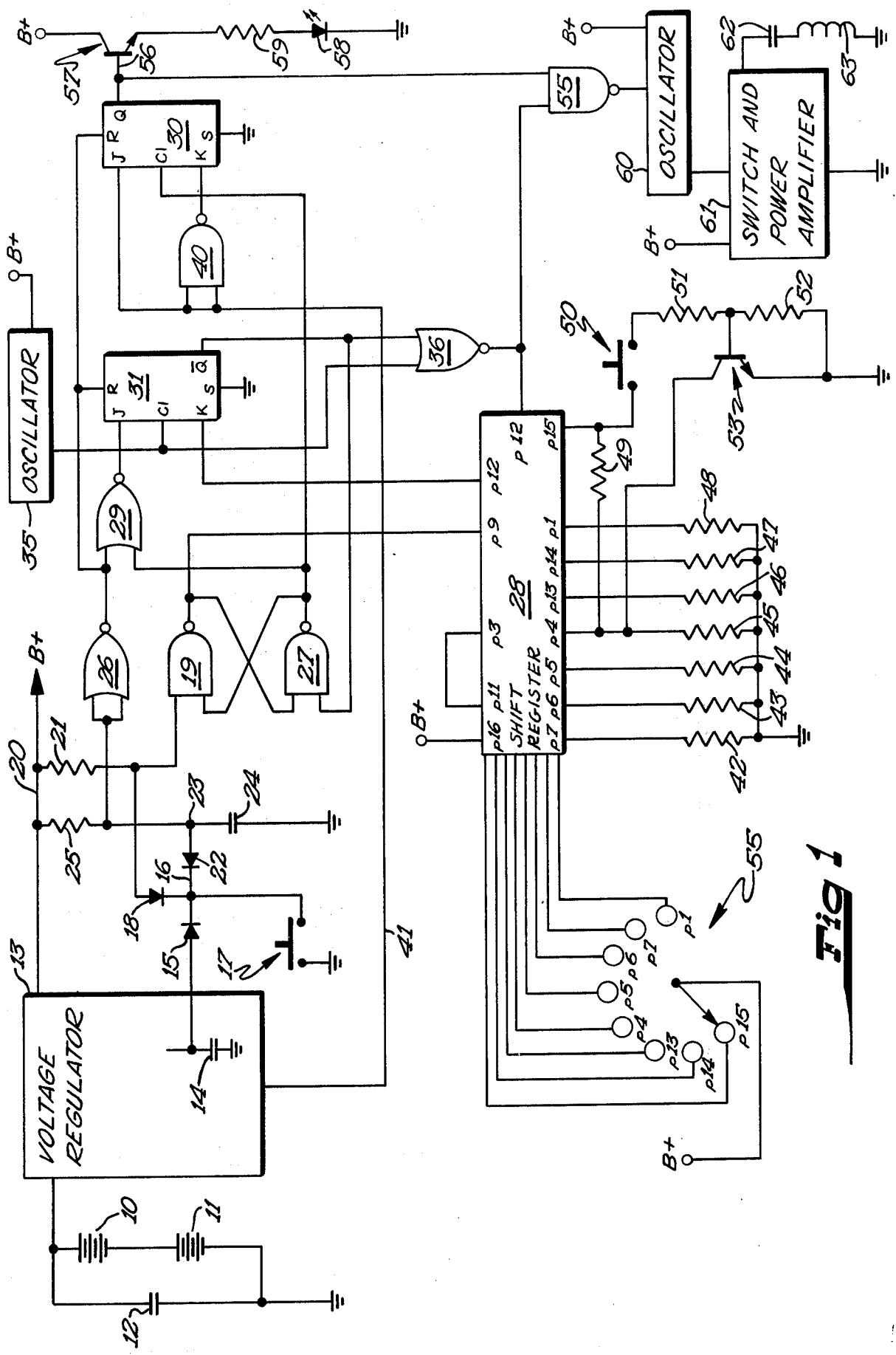
FIG. 1 illustrates a preferred embodiment of the present invention.

FIG. 1 illustrates a preferred embodiment of the non-invasive programming device of the present invention including a power supply consisting of two serially connected batteries 10 and 11, connected in parallel with a capacitor 12. A voltage regulator 13 is connected to the power supply and is designed to establish a substantially constant supply voltage output level for all power source voltage levels above a preselected level. That is, so long as the voltage level of the serially connected batteries 10 and 11 equals or exceeds a preselected value, the voltage regulator 13 will establish a substantially constant supply voltage (B+) approximating that preselected value. The positive output of the voltage regulator (B+) is applied by the regulator 13 to the line 20.

The voltage regulator 13 includes a capacitor 14 whose function will be more fully described below. For the present discussion, it is sufficient to indicate that when the capacitor 14 is fully charged the voltage regulator 13 is off. The capacitor 14 is connected via a diode 15 to a junction 16, with the junction 16 being connected to ground via a push-button switch 17. The junction 16 is similarly connected via a diode 18 to one input of a NAND gate 19 and to the positive voltage supply line 20 via a resistor 21. A diode 22 connects the junction 16 to a junction 23, the junction 23 being connected to ground via a capacitor 24, to the positive supply voltage line 20 via a resistor 25 and to both inputs of a NOR gate 26. The NAND gate 19 forms a latch, in known manner with a NAND gate 27, with the output of the NAND gate 19 being connected to a shift register 28 and the output of NAND gate 27 being connected as one input to a NOR gate 29 and to a clock input terminal of a JK flip-flop 30. The output of the NOR gate 26 is connected as the other input to the NOR gate 29 and to the reset terminals of the flip-flop 30 and another JK flip-flop 31.

An astable, free running square wave oscillator 35 has its output connected to the clock input terminal of flip-flop 31 and as one input to NOR gate 36. The set terminals of flip-flop 30 and 31 are both grounded and the $\overline{Q}$ terminal of flip-flop 31 is connected as the other inputs to NOR gate 36 and NAND gate 27.

In addition to establishing a substantially constant supply voltage level for all power source levels above a preselected value, the voltage regulator 13 generates a signal indicative of the establishment of the substantially constant supply voltage level. This supply voltage establishment signal is applied to the J terminal of flip-flop 30 and as both inputs to NAND gate 40 via a line 41. The output of NAND gate 40 is applied to the K terminal of flip-flop 30.

The shift register 28 is an 8 bit shift register of the type commonly termed "parallel in/serial out". One or more of the inputs of the shift register 28 may be "loaded" in a manner to be described below with the inputs being advanced or shifted through the various stages of the register in response to clock pulses. When the first loaded signal reaches the output stage of the shift register 28, flip-flop 31 is clocked to the low state and succeeding clock pulses are inhibited from the shift register by NOR gate 36. Thus, a loading of more than one stage of the shift register 28 is ineffective except as to the loading of the highest stage. It has been found advantageous to employ a shift register identified as RCA part number CD4021A which is described in RCA data book "COS/MOS Digital Integrated Circuits" on page 114 of the 1975 edition. The pin or terminal reference numerals preceded by a $p$ in FIG. 1, are those of the referenced RCA data book with the terminals $p7$, $p6$, $p5$, $p4$, $p13$, $p14$, $p1$ and $p15$ serving as input terminals, the terminal $p10$ serving as a clock terminal with the shift register 28 responding to the rising edge of a clock pulse and the terminal $p12$ serving as an output terminal. A "high" appearing on terminal $p9$ serves to load the shift register 28 while a "low" appearing at terminal $p9$ serves as a clock enable. Also, within this specific shift register, a loading on terminal $p14$ will be shifted to output terminal $p12$ on the first clock pulse, a loading on terminal $p13$ will be shifted to the terminal $p12$ on the second clock pulse and so on sequentially for a loading on input terminals $p4$, $p5$, $p6$, $p7$, $p1$ and $p15$. Thus, simultaneous loading of the shift register 28 at terminals $p4$ and $p15$ will result in a shifting of the signal applied at the terminal $p4$ to the output terminal $p12$ after three clock pulses at terminal $p10$ and a "shut off" of the shift register 28 to prevent a further shifting of the signal applied at the terminal $p15$.

The terminals $p7$, $p6$, $p5$, $p4$, $p13$, $p14$ and $p1$ of shift register 28 are connected to ground via a separate associated resistor 42–48, respectively. The terminal $p15$ of shift register 28 is connected to the terminal $p4$ by a resistance 49 and to ground through a push-button switch 50 and resistors 51 and 52. The input terminal p4 of shift register 28 is connected to ground through the base emitter junction of a transistor 53 and the base electrode 54 of transistor 53 is connected intermediate the resistances 51 and 52. A rotary switch 55 is provided with eight terminals each associated with one of the input terminals of the shift register 28 and is employed, in known manner, to apply the supply voltage appearing on line 20 to one of those input terminals. Additionally, when the rotary switch is in position to apply the supply voltage to pin $p15$ (as when the rotary switch is in the position illustrated in the FIG. 1), the supply voltage is also applied to input terminal $p4$ of shift register 28 via the resistance 49. Thus, a mere selection of terminal $p15$ will be inoperative inasmuch as terminal $p4$ will be also loaded and the signal at terminal $p4$ will be shifted to the output terminal $p12$ in fewer clock pulses than will the signal applied to terminal $p15$. However, by closing the push-button switch 50, the transistor 53 will turn on and shunt the signal appearing at input terminal $p4$ of shift register 28 while leaving that signal at input terminal $p15$. Thus, this interconnection of input terminals $p15$ and $p4$ can be employed to prevent an accidental selection of the number of pulses to be transmitted represented by pin $p15$, while allowing a selection of that number of pulses through a conscious manipulation of the push-button switch 50. This safeguard might be employed when the output parameter to be programmed is the repetition rate of an implanted cardiac pacemaker and the rate corresponding to a reception of eight pulses is below that which would be normally selected, 30 beats per minute, for example. Such a rate is below that generally regarded as being capable of sustaining life and a safeguard against its accidental selection is therefor desirable.

The output terminal $p12$ of shift register 28 is connected to the K terminal of flip-flop 31 and the output of the NOR gate 36 is connected to the terminal $p10$ of shift register 28 and as one input to NAND gate 55. The Q terminal of flip-flop 30 is connected as the other input to NAND gate 55 and to the base electrode 56 of the transistor 57. The emitter-collector junction of transistor 57 connects the positive voltage supply to a light emitting diode 58 via a resistor 59. The output of NAND gate 55 is applied to a gated oscillator 60 whose output is applied to switch and power amplifier 61. The switch and power amplifier 61 provides a low impedance source driving the LC series connection of capacitor 62 and inductor 63.

In operation, and assuming that capacitor 14 is fully charged to maintain voltage regulator 13 in the off condition, the push-button switch 17 is closed thereby discharging the capacitor 14 and rendering the voltage regulator 13 operative. Assuming that the power sources 10 and 11 are at or above a preselected voltage level, the voltage regulator 13 will establish a substantially constant supply voltage on the line 20 and generate a signal indicative of the establishment of that supply voltage level on line 41. The closing of the push-button switch 17 will also drain any charge on capacitor 24 thus applying a low to the inputs of NOR gate 26 causing its output to go high and reset the flip-flops 30 and 31. Similarly, closing of the push-button switch 17 applies a low to one input of the NAND gate 19 causing its output to go high and load the shift register 28, in accordance with the position of rotary switch 55, while the output of the NAND gate 27 goes low. Upon release of the push-button switch 17, the capacitor 14 begins to charge and will turn off the voltage regulator 13 when it becomes sufficiently charged in a manner to be described below. Similarly, the capacitor 24 will begin to charge through the resistor 25. After capacitor 24 has charged sufficiently, after 30 milliseconds, for example, it will function as a high input to both input terminals of NOR gate 26 resulting in a low output from NOR gate 26 and two low inputs to NOR gate 29. Thus, the output of NOR gate 29 will go high and be applied to the J terminal of flip-flop 31 causing the $\overline{Q}$ terminal of flip-flop 31 to go low on the rising edge of the next square wave pulse from oscillator 35. When the $\overline{Q}$ terminal of flip-flop 31 goes low, that low is applied as an input to NAND gate 27 causing its output to go high and serve as a clock pulse to the flip-flop 30 while the output to the NAND gate 19 will go low serving as a clock enable to the shift register 28. Prior to the output of the NAND gate 19 going low under the control of the $\overline{Q}$ terminal of flip-flop 31, its output was high which serves as a loading signal to the shift register 28 causing any signals applied to the input terminals of the shift register 28 to be loaded into the shift register 28. Also, with $\overline{Q}$ terminal of the flip-flop 31 low, the NOR gate 36 will produce a clock pulse at its output each time the output of oscillator 35 goes low with the shift register 28 responding to the rising edges of the clock pulses. When the loading of the shift register 28 has advanced to the output terminal $p12$ under control of the clock pulses appearing at the terminal $p10$, the terminal $p12$ will go high, and the $\overline{Q}$ terminal of flip-flop 31 will go high. With the $\overline{Q}$ terminal of flip-flop 31 high, one input of NOR gate 36 will be high thus preventing the passing of any additional clock pulses by NOR gate 36.

As stated above, upon establishment of a substantially constant supply voltage on positive power supply line 20, a signal representative of the establishment of that voltage level will be applied to line 41 and to the J terminal of flip-flop 30. Through the operation of the NAND gate 40, the inverse of that signal will be applied to the K terminal of flip-flop 30. Thus, with a high signal on line 41 representing the establishment of the predetermined supply voltage, the clock pulse to flip-flop 30 from the output of NAND gate 27 will cause the Q terminal of flip-flop 30 to go high and apply a high input to NAND gate 55 and turn on transistor 57. The turn on of transistor 57 applies the supply voltage across a light emitting diode 58 thus giving a visual indication of the establishment of the supply voltage level. Additionally, the high input to NAND gate 55 causes that gate to pass the inverse of the clock pulse appearing as the output of NOR gate 36. Conversely, however, if the Q terminal of flip-flop 30 should remain low, as a result of a failure to establish the reference voltage supply level, for example, the output of NAND gate 55 will remain high without regard to the input signals applied to it from the output of the NOR gate 36. It should be noted that once the reference voltage supply level has been established, the Q terminal of flip-flop 30 will remain high and allow the completion of the pulse transmission cycle. Thus, a subsequent decrease in the power supply voltage will not interrupt the transmission of the desired number of programming pulses and result in an alteration in output parameters to an undesired level.

As stated above, the oscillator 60 is a gated oscillator which may operate at 175 KHz, for example, in response to a low appearing as the output of NAND gate 55. The oscillations from triggered oscillator 60 are passed to switch and power amplifier 61 which alternately switches the capacitor 62 and inductor 63 between the positive supply voltage and g.ound thereby providing transmitted bursts of radio frequency energy at the frequency of the oscillator 60 and at the repetition rate of the oscillator 35, in known manner.

In functional terms, the device described in FIG. 1 includes a power supply, circuitry for generating a preselected number of control pulses, circuitry for transmitting a pulse of radio frequency energy on the occurrence of each control pulse, means for initiating the operation of the control pulse generator and means for enabling the power supply only during an interval of predetermined duration following the initiating of operation of control pulse generator. The power supply provides power for all of the operative elements and consists of a power source in the form of serially connected batteries 10 and 11 connected in parallel with a capacitor 12, the capacitor serving as a current backup for high current demand, in known manner, and a voltage regulator 13 for establishing a substantially constant supply voltage level for all power source levels above a preselected value. The control pulse generator includes the oscillator 35 as the source of the pulses and the shift register 28 as the means for preselecting their number. Operation of the control pulse generating system is initiated by closing the push-button switch 17 and reopening it with the voltage regulator 13 being enabled for a predetermined time following reopening of the push-button switch 17, the time being established by the charge time of the capacitor 14. Additionally, the voltage regulator 13 provides a signal indicative of the establishment of the substantially constant supply voltage level which signal is employed to give an indication of the establishment of that supply voltage level via the light emitting diode 58 as well as to prevent the transmission of any programming pulses, in the absence of the supply voltage establishment signal, via the NAND gates 55. The NAND gates 19 and 27, in combination with the NOR gate 29, function as a "no bounce" circuit for the push-button switch 17 and the time delay provided by the charging of capacitor 24 facilitates the operation of the "no bounce" circuit.

Figure 2:
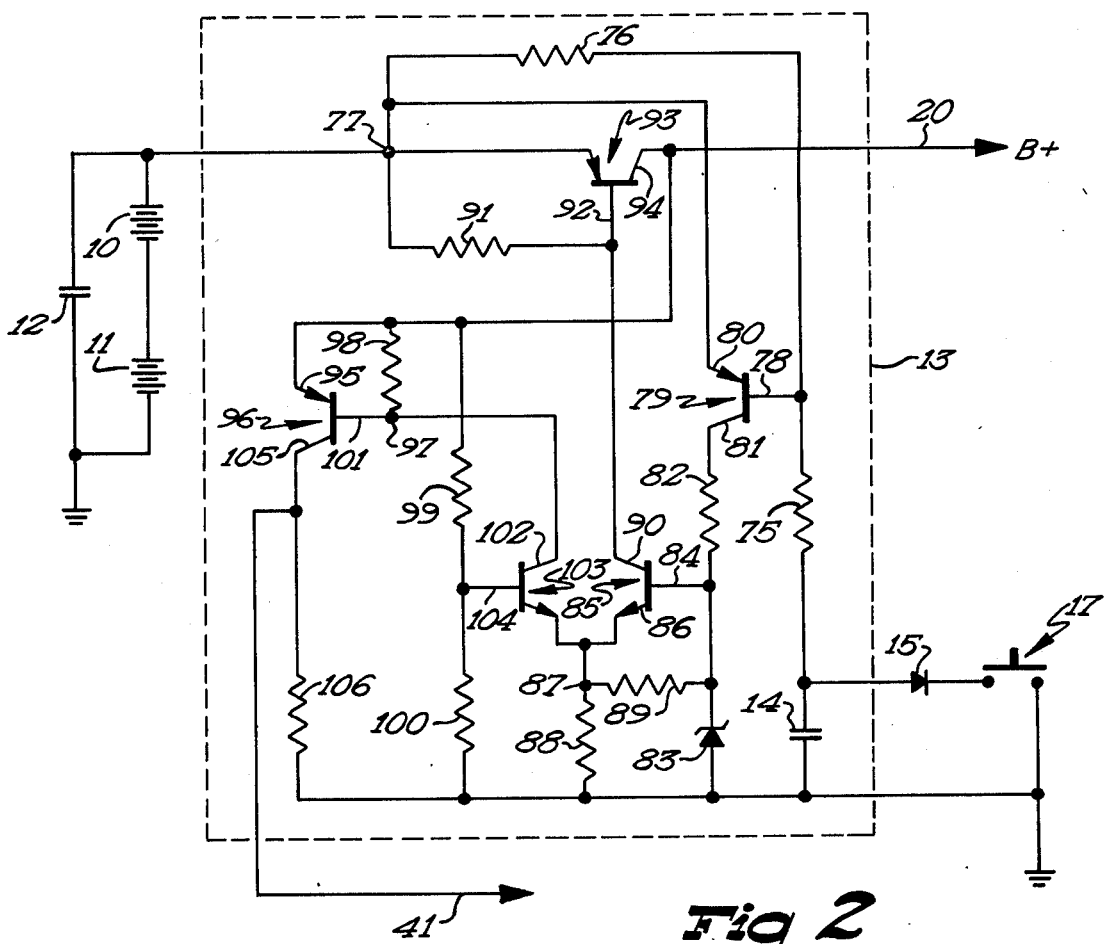
FIG. 2 illustrates a portion of the preferred embodiment of FIG. 1.

Referring now to FIG. 2, there is shown the power supply of the present invention including the power sources 10 and 11, the capacitor 12 and the voltage regulator 13. As discussed above, the voltage regulator 13 includes a capacitor 14 connected to the push-button switch 17 via a diode 15. Capacitor 14 is also connected to a junction 77 through resistors 75 and 76 with the junction 77 being connected to the power sources 10 and 11 and capacitor 12. The base electrode 78 of a transistor 79 is connected intermediate the resistances 75 and 76 while its emitter electrode 80 is connected to the junction 77. The collector electrode 81 of transistor 79 is connected to ground via the resistor 82 and zener diode 83. The base electrode 84 of a transistor 85 is connected intermediate the resistor 82 and diode 83 while its emitter electrode 86 is connected to a junction 87. The junction 87 is connected to ground via a resistor 88 and intermediate the resistor 82 and the diode 83 via a resistor 89. The collector electrode 90 of transistor 85 is connected to the junction 77 by a resistor 91 and to the base electrode 92 of a transistor 93. The emitter collector junction of transistor 93 connects the junction 77 to the line 20 while its collector electrode 94 is connected to the emitter electrode 95 of transistor 96, to junction 97 by resistor 98 and to ground through resistors 99 and 100. The junction 97 is connected to the base electrode 101 of transistor 96 and to the collector electrode 102 of transistor 103. The base electrode 104 of transistor 103 is connected intermediate the resistor 99 and 100 while the collector electrode 105 of transistor 96 is connected to the line 41 and to ground through a resistor 106.

In operation, and assuming that capacitor 14 is fully charged, all of the transistors within the voltage regulator 13 are off. Closing of the push-button switch 17 causes the capacitor 14 to discharge through the diode 15 and switch 17. Upon the discharge of capacitor 14, the transistor 79 will turn on to turn on transistor 85 and establish a reference potential at its base 84. Turn on of transistor 85 will induce a current in the base 92 of the transistor 93 causing it to turn on. The resistors 99 and 100 form a voltage divider and will apply a voltage to the base 104 of transistor 103 equal to the reference potential applied to the base 104 of transistor 85 when the transistor 93 has turned on sufficiently to establish a desired supply voltage level on the line 20. For example, assuming that the supply voltage level desired on line 20 is 12 volts, and the serially connected power sources 10 and 11 have a combined voltage in excess of 12 volts, then, transistor 93 will turn on sufficiently to apply 12 volts to the line 20 with the voltage divider formed at resistors 99 and 100 serving to apply a base voltage to transistor 103 equal to the reference potential applied to the base 84 of transistor 85. The reference potential may be selected to be 4.7 volts in the example given. Therefore, so long as the power level of the power sources 10 and 11 exceeds a predetermined value, the transistor 93 will turn on sufficiently to establish a substantially constant supply voltage on the line 20. Assuming the establishment of the desired supply voltage on line 20, the transistor 96 will turn on and apply that supply voltage to the line 41 which voltage will function as a supply voltage establishment signal as discussed above with reference to FIG. 1. However, assuming that the power level of the power sources 10 and 11 is not sufficient to establish the desired supply voltage on line 20, the voltage applied to the base 104 of transistor 103 will fall short of the reference potential applied to the base 84 of transistor 85 resulting in a failure of the transistor 96 to turn on and, ultimately, the transmission of any programming pulses. The transistor 79 and, thus, the remaining transistors of voltage regulator 13 will remain on after discharge of the capacitor 14 and until that capacitor has recharged. The capacitor 14 is discharged on closing of the push-button switch 17 and begins to recharge when that switch is re-opened. As discussed above, with reference to FIG. 1, operation of the "control pulse generating circuitry" is initiated on a reopening of the switch 17 and, thus, the charge time of capacitor 14 following a reopening of the push-button switch 17 maintains the voltage regulator 13 enabled for a predetermined period of time following the initiating of operation of the control pulse generating circuitry, the time being established by the capacitor 14 and resistances 75 and 76.

Figure 3:
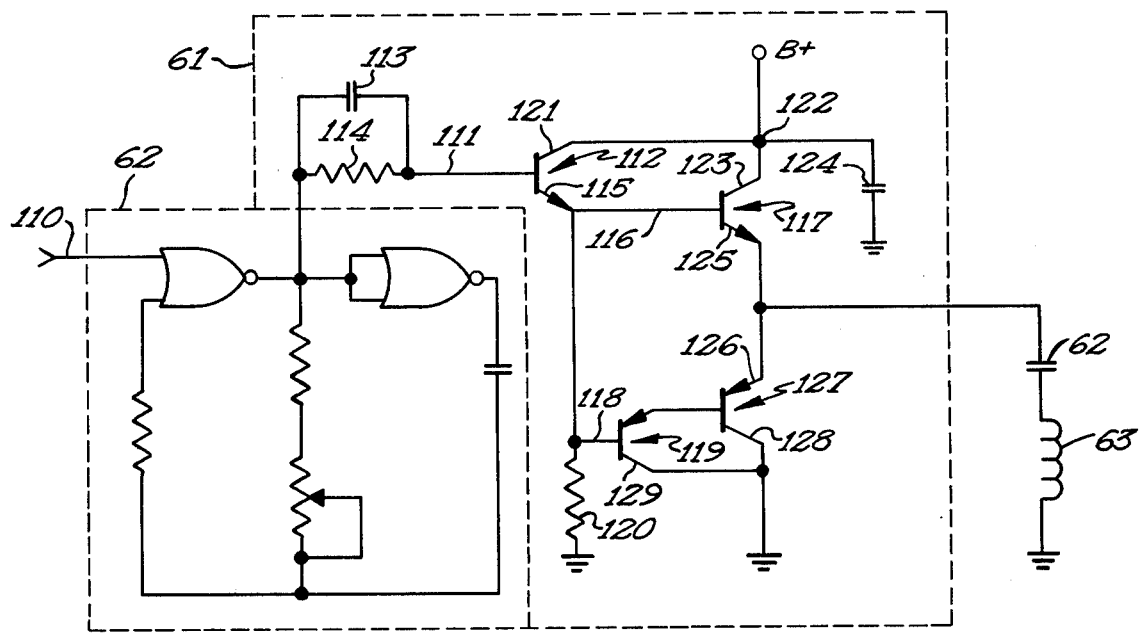
FIG. 3 illustrates another portion of the preferred embodiment of FIG. 1.

Referring now to FIG. 3 there is illustrated the pulse transmission circuitry discussed above with reference to FIG. 1 in the form of oscillator 60 and switch and power amplifier 61 connected to the capacitor 62 and inductor 63. As stated, the oscillator 60 is a gated oscillator which may advantageously operate at 175 KHz in response to a negative signal appearing on the line 110. Line 110 is the output of NAND gate 55 (see FIG. 1). The operation of gated oscillators such as that shown at 60 are well known to the prior art.

The output of oscillator 60 is applied to the base electrode 111 of transistor 112 through parallel connected capacitor 113 and resistors 114. The resistor 114 is a current limiting resistor while the capacitor 113 serves as a "speed up" capacitor, both of which are well known to the prior art. The emitter electrode 115 of transistor 112 is connected to the base electrode 116 of a transistor 117, to the base electrode 118 of a transistor 119 and to ground through a resistor 120. The collector electrode 121 of transistor 112 is connected to a junction 122, the junction being connected to the supply voltage, to the collector electrode 123 of transistor 117 and to ground by a capacitor 124. The emitter electrode 125 of transistor 117 is connected to the emitter electrode 126 of transistor 127 while the collector electrode 128 of transistor 127 and the collector electrode 129 of transistor 129 are connected to each other and to ground. The serially connected capacitor 62 and inductor 63 are connected intermediate the emitter electrodes 125 and 126 of transistors 117 and 127, respectively.

As illustrated, the switch and power amplifier 61 consists essentially of a complimentary Darlington connection of transistors 112, 117, 119, and 127. In this configuration, they operate as a low impedance source driving the LC series connection of capacitor 62 and inductor 63, the inductor 63 serving as a transmitting antennae in known manner. That is, a negative pulse appearing on line 110 of oscillator 60 will trigger that oscillator into operation while the switch and power amplifier 61 will operate under control of the oscillations from the oscillator 60 to alternately connect the positive power supply voltage and ground across the capacitor 62 and 63. The configuration illustrated will "ring up" to the amplitude necessary to penetrate the chest wall with a signal capable of being detected by an implantable device (approximately 200 volts).

From the above, it is apparent that the present invention provides a non-invasive programmer for an implanted body stimulator which reduces the drain on the power supply by enabling that power supply only during a limited time while giving a reliable indication of the adequacy of the power available from the power supply and preventing the transmission of programming pulses in the event that the power level of the power supply is inadequate. It has been found advantageous to construct the embodiment illustrated using components having the values and/or manufacturers part designation specified within the description or as given in the following table:

| Resistors | Ohms |
|---|---|
| 21, 42, 43, 44, 45, 46, 47, 48 | 1 meg |
| 25 | 510K |

-continued

| | |
|---|---|
| 49 | 10K |
| 51 | 330K |
| 52, 89, 91, 106 | 100K |
| 59, 82 | 620 |
| 75, 76 | 24K |
| 88 | 150 |
| 98 | 68 |
| 99 | 2000 |
| 100 | 1300 |
| 114, 120 | 6.2K |
| Capacitors | farads |
| 12 | 100 micro |
| 14 | 10 micro |
| 24, 124 | 0.1 micro |
| 62 | 1800 pico |
| 113 | 1200 pico |
| Antenna 63 | 46 turns of No. 30 wire equivalent to 680 microhenries |
| Diodes 15, 18, 22, 58 | IN914 |
| Diode 83 | IN750A |
| Transistors 53, 57, 85, 103, 112, 117 | 2N2222 |
| Transistors 79, 93, 96, 119, 127 | 2N2907 |
| NAND gates | RCA CD4011 |
| NOR gates | RCA CD4001 |
| Flip-flops | RCA CD4027 |
| Shift Register | RCA CD4021 |

It is therefore to be understood that, within the scope of the appended claims, the invention may be practiced otherwise than as specifically described.

What is claimed is:

1. In a device for programming an implantable body stimulator through transmitted pulses of radio frequency energy of the type having power supply means, means powered by said power supply means for generating a preselected transmitted signal of radio frequency energy and means for initiating the operation of said generating means, the improvement which comprises means responsive to said initiating means for enabling said power supply means during an interval of predetermined duration following the initiating of operation of said generating means.

2. The device of claim 1 wherein said power supply means comprises power source means and voltage regulator means for establishing a substantially constant supply voltage output level for all power source means output voltage levels above a preselected level, said enabling means comprising means for enabling said voltage regulator means.

3. The device of claim 2 further comprising means for indicating the establishment of said substantially constant supply voltage output level.

4. The device of claim 1 wherein said generating means comprises means for producing a preselected number of control pulses and means responsive to said control pulses for transmitting a pulse of radio frequency energy on the occurrence of each control pulse, said initiating means comprising means for initiating the operation of said control pulse producing means.

5. The device of claim 4 wherein said power supply means comprises power source means and voltage regulator means for establishing a substantially constant supply voltage output level for all power source means output voltage levels above a preselected level, said enabling means comprising means for enabling said voltage regulator means.

6. The device of claim 5 further comprising:
means for producing a signal indicative of the establishment of said substantially constant supply voltage output level; and
means for blocking said control pulses from said transmitting means in the absence of said supply voltage output level establishment signal.

7. The device of claim 6 wherein said means for producing a signal indicative of the establishment of said substantially constant supply voltage output level comprises means for maintaining the supply voltage output level establishment signal throughout said interval.

8. The device of claim 4 further comprising means for blocking said control pulses from said transmitting means when the output voltage level of said power supply means is lower than a predetermined level at the time of initiating the operation of said control pulse producing means.

9. The device of claim 4 further comprising means for gating said control pulses to said transmitting means throughout said interval when the output voltage level of said power supply means at least equals a predetermined level at the time of initiating the operation of said control pulse producing means.

10. The device of claim 1 further comprising means for disabling said generating means when the output voltage level of said power supply means is lower than a predetermined level at the time of initiating the operation of said generating means.

11. The device of claim 1 further comprising means for enabling said generating means only after the output voltage level of said power supply means at least equals a predetermined level.

12. The device of claim 11 wherein said enabling means comprises means for enabling said generating means throughout said interval without regard to power supply means output voltage levels subsequent to, and lower than, a power supply means output voltage level at least equal to said predetermined level.

13. A device for programming an implantable body stimulator having at least one alterable output characteristic and means responsive to transmitted pulses of radio frequency energy for altering said output characteristic in predetermined correspondence with the number of said transmitted pulses, said device comprising:
power source means;
voltage regulator means for establishing a substantially constant supply voltage output level for all power source means output voltage levels above a predetermined level;
means powered by said voltage regulator means for producing a preselected number of control pulses;
means powered by said voltage regulator means and responsive to said control pulses for transmitting a pulse of radio frequency energy on the occurrence of each control pulse;
means for enabling said voltage regulator means and initiating the operation of said control pulse producing means; and
means responsive to the establishing of said substantially constant supply voltage output level for gating said control pulses to said transmitting means only after enabling of said voltage regulators means and the establishment of said substantially constant supply voltage output level.

14. The device of claim 13 further comprising means for disabling said voltage regulator means after a predetermined period of time following initiating the operation of said control pulse producing means.

15. The device of claim 14 wherein said enabling and initiating means comprises switch means, said device further comprising no bounce means interconnecting said switch means and said control pulse producing means.

16. The device of claim 15 further comprising means for indicating the establishment of said substantially constant supply voltage output level.

17. The device of claim 14 wherein said means for gating comprises:
   means for producing a signal indicative of the establishment of said substantially constant supply voltage output level; and
   means enabled by said output level establishment signal, and operative throughout said predetermined period of time, for passing all of said control pulses subsequent to said output level establishment signal to said transmitting means.

18. The device of claim 13 wherein said gating means comprises:
   means for producing a signal indicative of the establishment of said substantially constant supply voltage output level; and
   means for blocking all of said control pulses from said transmitting means until the occurrence of said output level establishment signal.

* * * * *

UNITED STATES PATENT AND TRADEMARK OFFICE
CERTIFICATE OF CORRECTION

PATENT NO. : 4,024,875
DATED : May 24, 1977
INVENTOR(S) : James J. Putzke

It is certified that error appears in the above-identified patent and that said Letters Patent are hereby corrected as shown below:

Column 1, line 7, delete "present" and insert --preset--.

Column 6, line 48, delete "gates" and insert --gate--.

Column 8, line 16, delete "resistors" and insert --resistor--.

Signed and Sealed this

Fourth Day of October 1977

[SEAL]

Attest:

RUTH C. MASON
Attesting Officer

LUTRELLE F. PARKER
Acting Commissioner of Patents and Trademarl